(12) United States Patent
Fujimori et al.

(10) Patent No.: US 9,895,053 B2
(45) Date of Patent: Feb. 20, 2018

(54) CAPSULE TYPE MEDICAL DEVICE

(71) Applicant: OLYMPUS CORPORATION, Tokyo (JP)

(72) Inventors: Noriyuki Fujimori, Suwa (JP); Takatoshi Igarashi, Ina (JP); Yukiharu Makino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 541 days.

(21) Appl. No.: 14/191,677

(22) Filed: Feb. 27, 2014

(65) Prior Publication Data

US 2014/0180040 A1    Jun. 26, 2014

Related U.S. Application Data

(63) Continuation of application No. PCT/JP2012/063133, filed on May 23, 2012.

(30) Foreign Application Priority Data

Aug. 31, 2011   (JP) .................................. 2011-189704

(51) Int. Cl.
  *A61B 5/07*  (2006.01)
  *A61B 1/04*  (2006.01)
  (Continued)

(52) U.S. Cl.
  CPC .......... *A61B 1/041* (2013.01); *A61B 1/00016* (2013.01); *A61B 5/073* (2013.01);
  (Continued)

(58) Field of Classification Search
  CPC ....... A61B 1/04; A61B 1/00016; A61B 5/073; A61B 1/041; A61B 5/6861; A61B 2562/162; A61B 1/051
  See application file for complete search history.

(56) References Cited

U.S. PATENT DOCUMENTS

2003/0181788 A1    9/2003  Yokoi et al.
2006/0241422 A1*  10/2006  Muratayev ......... A61B 1/00016
                                                600/435
(Continued)

FOREIGN PATENT DOCUMENTS

EP        2092872 A1    8/2009
JP      2005-130943 A    5/2005
(Continued)

OTHER PUBLICATIONS

Extended Supplementary European Search Report dated May 20, 2015 from related European Application 12 82 6757.2.
(Continued)

*Primary Examiner* — Navin Natnithithadha
*Assistant Examiner* — Eric Messersmith
(74) *Attorney, Agent, or Firm* — Scully, Scott, Murphy & Presser, P.C.

(57) ABSTRACT

In a capsule endoscope, on an inside of a capsule type housing including a cylindrical main body section and two semispherical end cover sections and having a rotationally symmetrical shape with respect to a center axis of the housing, an image pickup board section, a transmission board section, and a reception board section are housed such that principal planes of the image pickup board section, the transmission board section, and the reception board section are orthogonal to the center axis. A coil wire of at least one of a transmission coil formed by a transmission coil wire and a reception coil formed by a reception coil wire, respective principal planes of which are orthogonal to the center axis, is disposed on the end cover section side of the housing.

7 Claims, 4 Drawing Sheets

(51) Int. Cl.
*A61B 1/00* (2006.01)
*A61B 5/00* (2006.01)
*A61B 1/05* (2006.01)

(52) U.S. Cl.
CPC .............. *A61B 1/051* (2013.01); *A61B 5/6861* (2013.01); *A61B 2562/162* (2013.01)

(56) References Cited

U.S. PATENT DOCUMENTS

| | | | |
|---|---|---|---|
| 2008/0139882 A1* | 6/2008 | Fujimori | A61B 1/041 600/109 |
| 2008/0227394 A1* | 9/2008 | Homan | A61B 1/00016 455/41.3 |
| 2008/0242931 A1* | 10/2008 | Nishino | A61B 1/00016 600/117 |
| 2008/0312501 A1 | 12/2008 | Hasegawa et al. | |
| 2009/0281382 A1 | 11/2009 | Takenaka et al. | |
| 2009/0281401 A1* | 11/2009 | Takenaka | A61B 1/00016 600/302 |
| 2010/0016670 A1* | 1/2010 | Segawa | A61B 1/041 600/165 |

FOREIGN PATENT DOCUMENTS

| | | |
|---|---|---|
| JP | 2006-280940 A | 10/2006 |
| JP | 2008-142410 A | 6/2008 |
| JP | 2009-060925 A | 3/2009 |
| WO | WO 2008072420 A1 | 6/2008 |

OTHER PUBLICATIONS

International Search Report dated Jul. 3, 2012 issued in PCT/JP2012/063133.

* cited by examiner

CAPSULE TYPE MEDICAL DEVICE

CROSS REFERENCE TO RELATED APPLICATION

This application is a continuation application of PCT/JP2012/063133 filed on May 23, 2012 and claims benefit of Japanese Application No. 2011-189704 filed in Japan on Aug. 31, 2011, the entire contents of which are incorporated herein by this reference.

BACKGROUND OF INVENTION

1. Field of the Invention

Embodiments of the present invention relate to a capsule type medical device introduced into a body and, more particularly, to a capsule type medical device including a reception coil for receiving an external signal and a transmission coil for transmitting information acquired in the body to an outside as an information signal.

2. Description of the Related Art

In recent years, a capsule endoscope including an image pickup function and a radio transmission function has emerged in the market. After being swallowed by an examinee, the capsule endoscope moves on insides of digestive tracts such as a stomach and a small intestine following a peristaltic movement and picks up images of insides of organs using the image pickup function until the capsule endoscope is naturally discharged.

Images picked up by the capsule endoscope while the capsule endoscope moves in the digestive tracts are transmitted to an external device provided on an outside of a subject as an image signal by the radio transmission function and stored in a memory of the external device. After swallowing the capsule endoscope, the examinee can freely act by carrying the external device including a radio reception function and a memory function. After observation by the capsule endoscope, the images stored in the memory of the external device are displayed on a display or the like and diagnosis or the like is performed.

Japanese Patent Application Laid-Open Publication No. 2006-280940 discloses a capsule endoscope in which an antenna formed by a transmission coil for radio transmission is embedded in a wiring board. Note that the antenna is also disposed in a center of a capsule type housing.

SUMMARY OF THE INVENTION

According to an aspect of the present invention, there is provided a capsule type medical device including: an information acquisition board section on which an information acquiring section configured to acquire in vivo information is disposed; a transmission board section on which a transmitting section configured to transmit the in vivo information as an information signal by radio is disposed; and a reception board section on which a receiving section configured to process an inputted external signal is disposed. The information acquisition board section, the transmission board section, and the reception board section are housed on an inside of a capsule type housing, which includes a cylindrical main body section and two semispherical end cover sections and having a rotationally symmetrical shape with respect to a center axis of the housing, such that principal planes of the information acquisition board section, the transmission board section, and the reception board section are orthogonal to the center axis. A coil wire of at least one of a transmission coil formed by a transmission coil wire for transmitting the information signal and a reception coil formed by a reception coil wire for receiving the external signal, respective principal planes of which are orthogonal to the center axis, is disposed on the end cover side of the housing.

DETAILED DESCRIPTION OF THE PREFERRED EMBODIMENT(S)

First Embodiment

Figure 1:
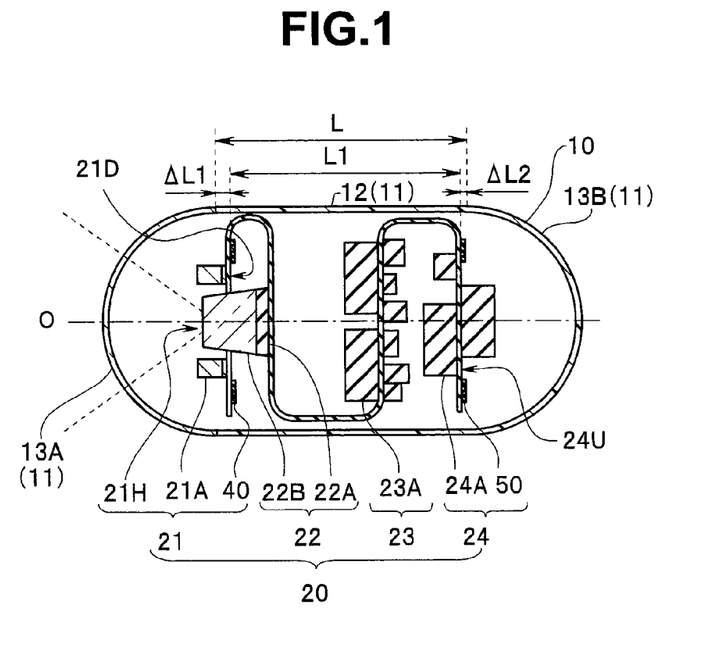
FIG. 1 is a sectional view of a capsule endoscope in a first embodiment.
Figure 2:
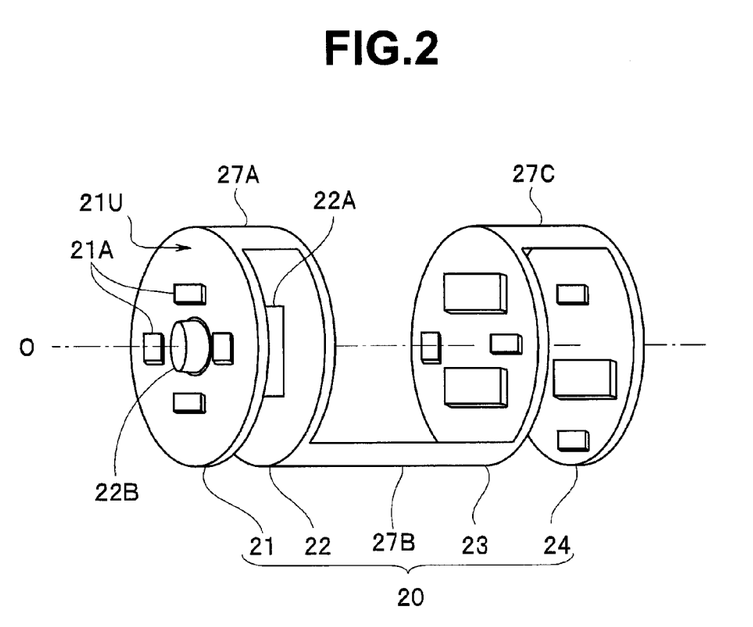
FIG. 2 is a perspective view for explaining a circuit board of the capsule endoscope in the first embodiment.

As shown in FIG. 1 and FIG. 2, in a capsule endoscope (hereinafter referred to as "endoscope") 10, which is a capsule type medical device in the present embodiment, a circuit board 20 including a plurality of substantially circular board sections is housed and sealed on an inside of a capsule type housing 11 in a bent state.

The endoscope 10 is a device introduced into a subject that, after being swallowed by an examinee, photographs images in a body at a predetermined time interval. The endoscope 10 is capable of not only transmitting image data acquired in the body to an outside by radio but also receiving a signal from the outside and performing control based on the signal.

The housing 11 includes a cylindrical main body section 12 and substantially semispherical end cover sections 13A and 13B at both ends of the main body section 12. The end cover section 13A is made of a transparent material. The main body section 12 and the end cover section 13B are made of an opaque material. However, the main body section 12 and the end cover section 13B may be integrally molded. The elongated housing 11 has a rotationally symmetrical shape having a center axis O in a longitudinal direction as an axis of rotational symmetry. Length L of the main body section 12 in a direction of the center axis O is 10 to 30 mm A diameter D in an orthogonal direction of the center axis O is 5 to 15 mm.

The circuit board 20 is a flexible wiring board on which a lighting board section 21, an image pickup board section 22, a transmission board section 23, and a reception board section 24, which respectively have substantially circular shapes, are coupled by connecting sections 27A, 27B, and 27C, which respectively have substantially rectangular shapes. The flat circuit board 20 is housed on an inside of the housing 11 such that the connecting sections 27 are bent 180 degrees together with spacer members (not shown in the figures) for determining an arrangement of the respective board sections and respective principal planes of the circuit board 20 are orthogonal to the center axis.

Note that a battery and a magnet not shown in the figures are also housed on the inside of the housing 11. The battery is a power supply source. The magnet is arranged in order to control an image pickup direction of the endoscope 10 using an external magnetic field. When a direct-current magnetic field is applied to the magnet from an outside, the magnet changes a posture of the housing 11 such that a magnetization direction becomes parallel to a line of magnetic force from the outside.

On a front surface 21U of the lighting board section 21, a plurality of light emitting elements, for example, four LEDs (21A) are respectively mounted on LED mounting lands 21AB, which are made of metal such as copper, around a substantially circular opening 21H. In the following explanation, a front surface of the circuit board 20 refers to a surface on which the LEDs (21A) are disposed.

As explained in detail below, a transmission coil 40 is disposed on a rear surface 21D of the lighting board section 21. A reception coil 50 is disposed on a front surface 24U of the reception board section 24.

On the image pickup board section 22, which is an information acquisition board section, an image pickup chip 22A, which is an image pickup section, is disposed with an image pickup surface directed to the opening 21H. A lens unit 22B is arranged on the image pickup surface of the image pickup chip 22A. The image pickup chip 22A is an information acquiring section configured to acquire an endoscopic image, which is in vivo information. On the transmission board section 23, a transmitting section 23A configured to transmit image data acquired by the image pickup chip 22A as an image signal (an information signal) by radio via the transmission coil 40 is disposed. On the reception board section 24, a receiving section 24A configured to receive an external signal via the reception coil 50 and process the external signal is disposed. For example, the external signal is an alternating magnetic field signal. The endoscope 10 drives a frequency dividing circuit with a pulse signal obtained by rectifying the received external signal and controls ON and OFF of power supply to internal circuits of the image pickup chip 22A, the LEDs (21A), the transmitting section 23A, and the like. A plurality of wires (not shown in the figures) for electrically connecting the respective board sections are formed in the connecting sections 27A to 27C.

Figure 3A:
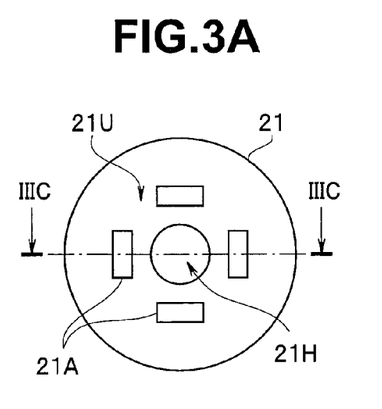
FIG. 3A is a diagram showing a front surface for explaining a lighting board section of the capsule endoscope in the first embodiment.
Figure 3B:
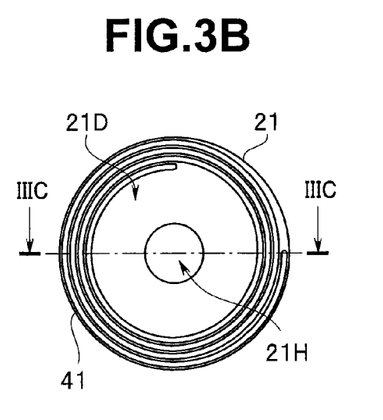
FIG. 3B is a diagram showing a rear surface for explaining the lighting board section of the capsule endoscope in the first embodiment.
Figure 3C:
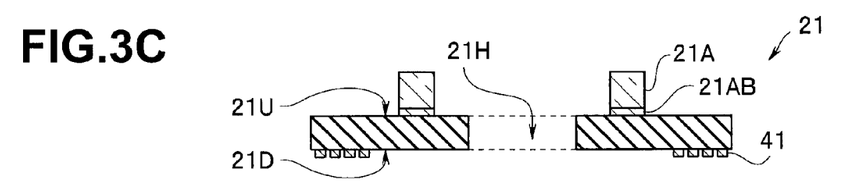
FIG. 3C is a sectional view taken along line IIIC-IIIC of FIG. 3A and FIG. 3B for explaining the lighting board section of the capsule endoscope in the first embodiment.

As shown in FIG. 3A to FIG. 3C, the transmission coil 40 disposed on the rear surface 21D of the lighting board section 21 is a spiral plane coil formed by a spiral transmission coil wire 41 and having a principal plane orthogonal to the center axis O. Like the transmission coil 40, the reception coil 50 disposed on the front surface 24U of the reception board section 24 is a spiral plane coil formed by a spiral reception coil wire (not shown in the figures) and having a principal plane orthogonal to the center axis O. Note that the principal plane of the plane coil means a principal plane of a base on which the coil wire is formed.

The transmission coil wire 41 and the reception coil wire made of a conductive material such as copper are manufactured simultaneously with manufacturing of connection lands for electronic component mounting, for example, the LED mounting lands 21AB. That is, the transmission coil wire 41 and the like are manufactured using a normal formation method (an additive method, a subtractive method, etc.) in which photolithography is used. Note that the coil wires may be manufactured by winding a coated conductive wire on a plane. Manufacturing methods, the sizes, the numbers of turns, and the like of the transmission coil 40 and the reception coil 50, which have different transmission and reception frequencies, may be different.

In the endoscope 10, the transmission coil 40 and the reception coil 50 are disposed on the end covers 13A and 13B sides of the housing 11. That is, as shown in FIG. 1, the transmission coil 40 is disposed in a position at a distance $\Delta L1$ from one end of the main body section 12 and the reception coil 50 is disposed in a position at a distance $\Delta L2$ from the other end of the main body section 12. $\Delta L1$ and $\Delta L2$ are equal to or smaller than 20% of L and preferably equal to or smaller than 10% of L.

The battery, the magnet, the electronic components mounted on the circuit board 20, and the like are electromagnetism shields and adversely affect transmission and reception of a radio signal. However, the transmission coil 40 and the reception coil 50 disposed on end sides of the main body section 12 where $\Delta L1$ and $\Delta L2$ are equal to or smaller than the range are less easily affected by the mounted components and the like. Further, a distance L1 between the transmission coil 40 and the reception coil 50 is equal to or larger than $(L-\Delta L1-\Delta L2)=(0.80 \times L)$ and preferably equal to or larger than $(0.90 \times L)$.

Note that the transmission coil 40 or the reception coil 50 may be disposed on an inside of the end cover section 13A or 13B. That is, the end covers 13A and 13B sides of the housing 11 include main body section sides of the end cover sections 13A and 13B in addition to end sides of the main body section 12. When the transmission coil 40 or the reception coil 50 is disposed on the inside of the end cover section 13A or 13B, L<L1. In the distance L1, a sign of $\Delta L1$ and $\Delta L2$ can be regarded as minus.

In the capsule endoscope including the transmission coil and the reception coil, when the transmission coil and the reception coil interfere with each other, it is likely that transmission and reception efficiency is deteriorated. However, even if the endoscope 10 is a capsule endoscope having small length L, it is possible to minimize an influence of mutual interference of the transmission coil 40 and the reception coil 50.

Therefore, transmission and reception of the endoscope 10 is efficient.

Note that a frequency of the image signal and a frequency of the external signal are different. When influences by harmonics and subharmonics are taken into account as well, it is particularly preferable that the frequency of the image signal and the frequency of the external signal not be an integral multiple or fraction having one as the numerator over an integer of each other.

In the endoscope 10, in order to obtain a maximum effect, the transmission coil 40 and the reception coil 50 are disposed at both the ends of the main body section 12. However, if the coil wire of one of the transmission coil 40 and the reception coil 50 is disposed on the lighting board section 21 at the end, it is possible to obtain a predetermined effect. In this case, the distance L1 between the transmission coil 40 and the reception coil 50 is preferably equal to or larger than (0.50×L).

An alternating magnetic field may be received and rectified by the reception coil 50 to obtain electric power of the endoscope 10. An endoscope that uses received power as driving power does not need to incorporate a battery. Since there is no limitation on a driving time due to a battery capacity, an in vivo observation for a long time is possible. In an endoscope incorporating a secondary battery, when a battery capacity decreases, it is possible to charge the secondary battery by receiving an external magnetic field signal.

Note that the LEDs (21A) mounted on the lighting board section 21 are elements that generate heat. The transmission coil wire 41 manufactured on the lighting board section 21 is made of a metal material having high conductivity such as copper. Therefore, the transmission coil wire 41 has not only a transmission and reception function but also a heat radiation function. Even if the LEDs (21A) generate heat, an operation of the endoscope 10 is stable because heat radiation is accelerated via the transmission coil wire 41.

Modifications of the First Embodiment

Next, modifications of the first embodiment are explained. Endoscopes in the modifications are similar to the endoscope 10 in the first embodiment. Therefore, the same components are denoted by the same reference numerals and signs and explanation of the components is omitted.

Figure 4A:
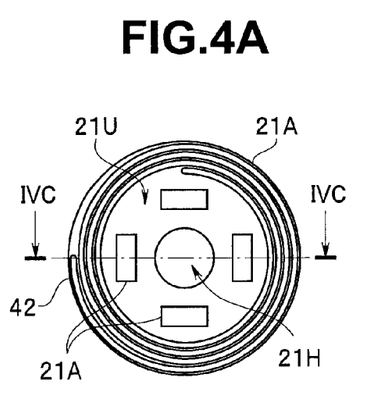
FIG. 4A is a diagram showing a front surface for explaining a lighting board section of a capsule endoscope in a modification 1 of the first embodiment.
Figure 4B:
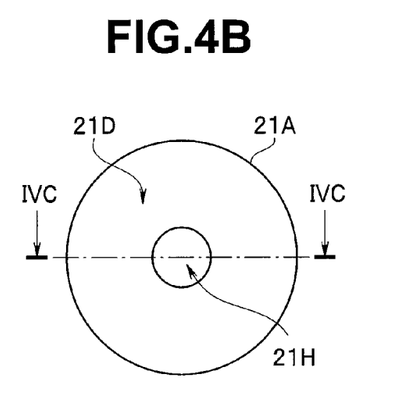
FIG. 4B is a diagram showing a rear surface for explaining the lighting board section of the capsule endoscope in the modification 1 of the first embodiment.
Figure 4C:
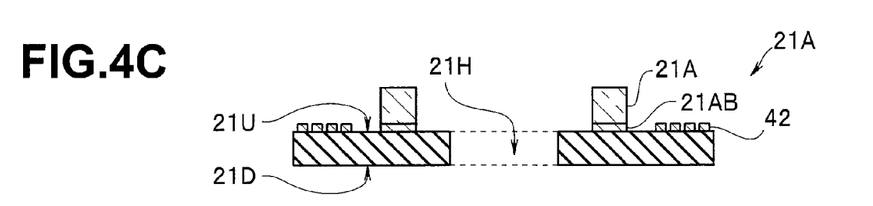
FIG. 4C is a sectional view taken along line VIC-VIC of FIG. 4A and FIG. 4B for explaining the lighting board section of the capsule endoscope in the modification 1 of the first embodiment.

As shown in FIG. 4A to FIG. 4C, in an endoscope in a modification 1, a coil wire 42 of the transmission coil 40 is disposed in an outer circumferential region of the four LEDs (21A) disposed on the front surface 21U of a lighting board section 21A.

Figure 5A:
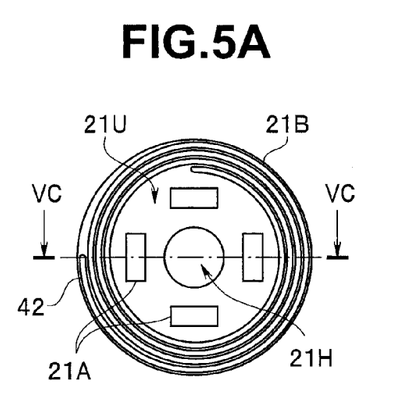
FIG. 5A is a diagram showing a front surface for explaining a lighting board section of a capsule endoscope in a modification 2 of the first embodiment.
Figure 5B:
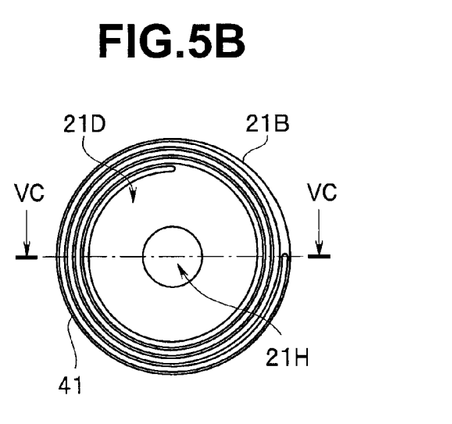
FIG. 5B is a diagram showing a rear surface for explaining the lighting board section of the capsule endoscope in the modification 2 of the first embodiment.
Figure 5C:
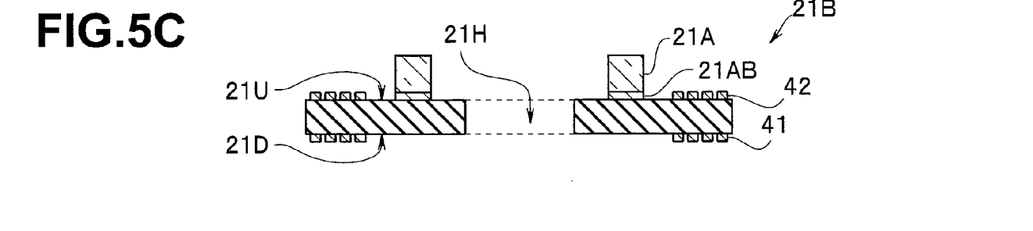
FIG. 5C is a sectional view taken along line VC-VC of FIG. 5A and FIG. 5B for explaining the lighting board section of the capsule endoscope in the modification 2 of the first embodiment.

As shown in FIG. 5A to FIG. 5C, in an endoscope in a modification 2, the transmission coil 40 includes the transmission coil wire 41 disposed on the rear surface 21D of a lighting board section 21B and a transmission coil wire 42 disposed on the front surface 21U. The transmission coil wire 41 and the transmission coil wire 42 are connected by a through board wire. Note that the transmission coil wire 41 and the transmission coil wire 42 shown in FIG. 5A to FIG. 5C have substantially the same shapes. However, the transmission coil wire 41 may be wound to a further inner circumferential section. A transmission coil including coil wires on both surfaces of a board section has a large number of times of winding (number of turns). Therefore, transmission and reception efficiency of the transmission coil is high.

Note that a disposing position of the transmission coil 40 including a plurality of plane coils is regarded as a center of positions of a plurality of plane coil wires, for example, a center in a thickness direction of the lighting board section 21B.

Figure 6:
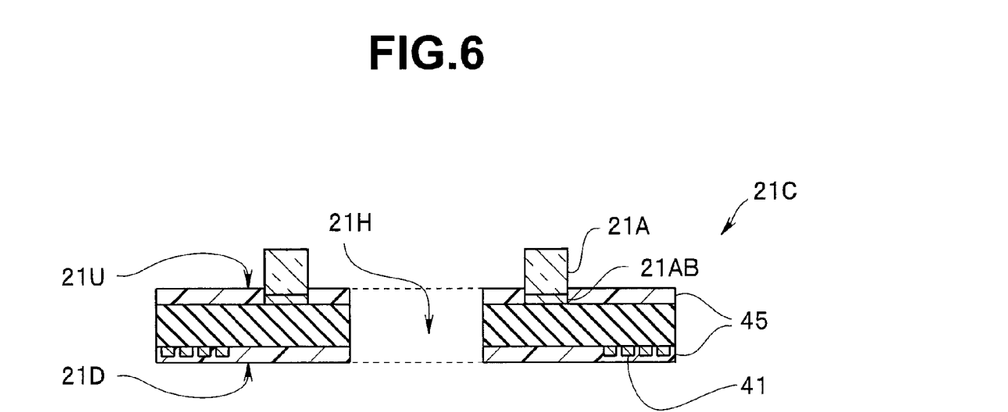
FIG. 6 is a sectional view of a lighting board section of a capsule endoscope in a modification 3 of the first embodiment.

As shown in FIG. 6, the transmission coil 40 of an endoscope in a modification 3 includes an insulating layer 45 configured to cover the transmission coil wire 41 disposed on the rear surface 21D of a lighting board section 21C. The insulating layer 45 manufactured using an insulative resin solution or an insulative sheet contributes to improvement of reliability of the transmission coil wire 41.

Figure 7:
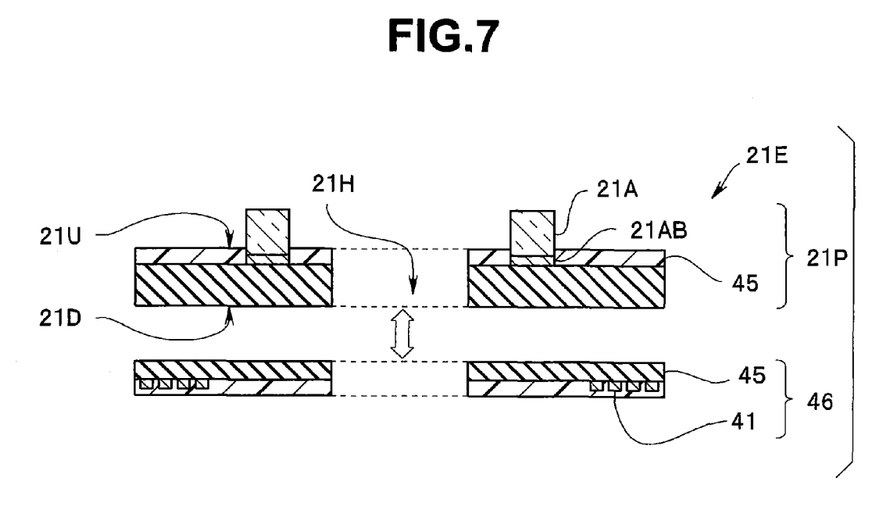
FIG. 7 is a sectional view of a lighting board section of a capsule endoscope in a modification 4 of the first embodiment.

As shown in FIG. 7, in an endoscope in a modification 4, in a lighting board section 21E, a coil board section 46, in a center of which the transmission coil wire 41 including a substantially circular opening having the same size as the opening 21H is disposed, is bonded to the rear surface 21D of a lighting board section 21P via, for example, an adhesive and integrated.

The coil board section 46 can be manufactured separately from the circuit board 20. Therefore, the manufacturing of the coil board section 46 is easy. In order to further increase the number of turns, coil wires may be manufactured on both surfaces of the coil board section 46. The coil board section 46 including a coil wire on one surface or including coil wires on both surfaces may be joined to the lighting board section 21P including a coil wire on one surface or including coil wires on both surfaces.

Note that it is preferable that the transmission coil wire 41 on the rear surface 21D of the lighting board section 21P is not disposed right under the LED mounting lands 21AB disposed on the front surface 21U. This is because it is likely that the LED mounting lands 21AB made of metal interfere with the transmission coil wire 41. However, the above does not apply, in particular, in a small-diameter capsule endoscope.

Note that the transmission coil 40 in the modifications is explained. However, the same configuration can be used in the reception coil 50 as well. For example, a reception coil wire may be formed on a rear surface of the reception board section 24. Reception coil wires may be formed on both surfaces of the reception board section 24. A reception coil board may be joined to the rear surface of the reception board section 24.

A plurality of board sections may be an integral board section. For example, the transmission board section 23 and the reception board section 24 may be an integral transmission and reception board section.

Second Embodiment

An endoscope 10A in a second embodiment is explained. The endoscope 10A is similar to the endoscope 10 in the first embodiment. Therefore, the same components are denoted by the same reference numerals and signs and explanation of the components is omitted.

Figure 8:
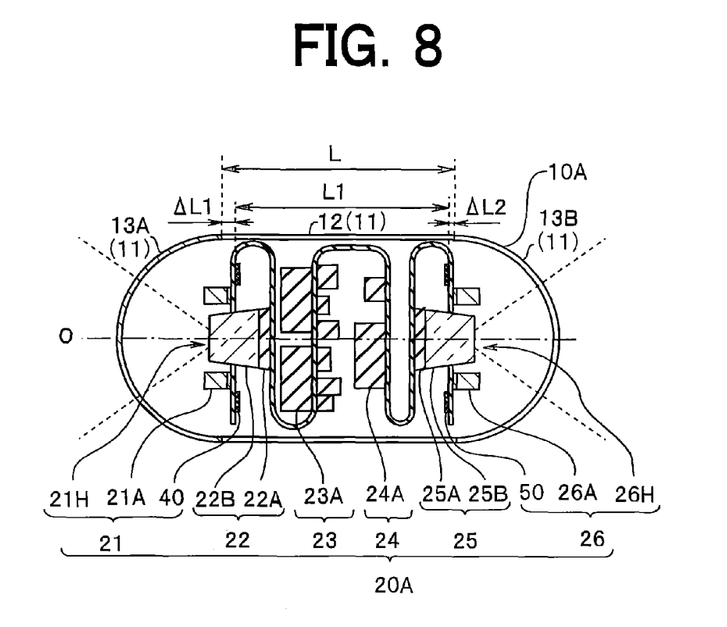
FIG. 8 is a sectional view of a capsule endoscope in a second embodiment.

As shown in FIG. 8, the endoscope 10A is a so-called binocular type including two image pickup chips 22A and 25A configured to photograph visual fields in opposite directions to each other.

As shown in FIG. 8, a circuit board 20A of the endoscope 10A is configured by arranging, in a row, the first lighting board section 21, the first image pickup board section 22, the transmission board section 23, the reception board section 24, a second image pickup board section 25, and a second lighting board section 26 in order via connecting sections thereof.

The first lighting board section 21 and the second lighting board section 26 have substantially the same configurations.

The first image pickup board section 22 and the second image pickup board section 25 also have substantially the same configurations.

The two image pickup chips 22A and 25A of the endoscope 10A of the binocular type are disposed such that image pickup directions thereof are opposite directions along the center axis O of the housing 11.

In the endoscope 10A, the transmission coil 40 is disposed on the first lighting board section 21 arranged at an end of the main body section 12. The reception coil 50 is disposed on the second lighting board section 26 arranged at the other end.

The endoscope 10A in the present embodiment has an effect same as the effect of the endoscope 10 and is the binocular type.

Note that, in the endoscope 10A, the explained configurations of the modification of the endoscope 10 can be used. The first lighting board section 21 and the second lighting board section 26 may be configured differently.

In the above explanation, the capsule endoscope is explained as an example. However, the same effect is provided with various capsule type medical devices such as a capsule type medical device for digestive fluid sampling, a pH sensor of a swallow type, and a drug delivery system.

The present invention is not limited to the embodiments explained above and various alterations, modifications, and the like are possible in a range in which the gist of the present invention is not changed.

What is claimed is:

1. A capsule type medical device comprising:
    a capsule type housing comprising a cylindrical main body section and two cover sections arranged at two ends of the cylindrical main body, wherein the capsule type housing has a rotationally symmetrical shape with respect to a center axis extending between a first end and a second end;
    a flexible wiring board comprising:
        a first board section;
        a first image pickup chip arranged to the first board section, wherein the first image pickup chip is configured to acquire a first image data;
        a second board section coupled to the first board section;
        an information signal generating circuit arranged to the second board section, wherein the information signal generating circuit is configured to generate an information signal based on the first image data; in vivo information;
        a third board section coupled to the second board section;
        a received signal processing circuit arranged to the third board section, wherein the received signal processing circuit is configured to process an external signal;
        a fourth board section; and
        a first plurality of light emitting elements arranged to the fourth board section, wherein the first plurality of light emitting elements are configured to light an image pickup visual field of the first image pickup chip,
    wherein the flexible wiring board is arranged within the capsule type housing such that:
        a principal plane of the first board section, a principal plane of the second board section and a principal plane of the third board section are arranged to intersect the center axis,
        the fourth board section is arranged to be closer to the first end than the first board section, the second board section and the third board section, and
        the first plurality of light emitting elements are disposed on a first surface of the fourth board section to face the first end;
    a transmission coil configured to transmit the information signal; and
    a reception coil disposed on the fourth board section, wherein the reception coil is configured to receive the external signal,
    wherein the transmission coil and the reception coil are arranged within the capsule type housing such that the first board section, the second board section and the third board section are arranged between the transmission coil and the reception coil along the center axis.

2. The capsule type medical device according to claim 1, further comprising:
    wherein the flexible wiring board further comprises:
        a fifth board section;
        a second image pickup chip arranged to the fifth board section, wherein the second image pickup chip is configured to acquire a second image data, wherein the first image pickup chip is arranged to acquire the first image data in a first direction, and the second image pickup chip is arranged to acquire the second image data in a second direction different from the first direction;
        a sixth board section; and
        a second plurality of light emitting elements arranged to the sixth board section, wherein the second plurality of light emitting elements are configured to light an image pickup visual field of the second image pickup chip,
    wherein the fourth board section and the sixth board section are arranged within the capsule housing such that the first board section, the second board section, the third board section and the fifth board section are arranged between the fourth board section and the sixth board section along the center axis, and
    wherein the transmission coil and is arranged on the sixth board section.

3. The capsule type medical device according to claim 1, wherein the reception coil is disposed on a second surface of the fourth board section to face the second end.

4. The capsule type medical device according to claim 1, wherein the reception coil is disposed on the first surface of the fourth board section to surround the first plurality of light emitting elements.

5. The capsule type medical device according to claim 1, further comprising an insulating layer configured to cover the reception coil disposed on the fourth board section.

6. The capsule type medical device according to claim 1, further comprising a coil board on which the reception coil is disposed, wherein the coil board is arranged to a second surface of the fourth board section to face the second end.

7. The capsule type medical device according to claim 1, wherein a distance between the transmission coil and the reception coil is equal to or larger than 0.8 L with respect to a length L of the main body section along the center axis.

* * * * *

UNITED STATES PATENT AND TRADEMARK OFFICE
CERTIFICATE OF CORRECTION

PATENT NO. : 9,895,053 B2  
APPLICATION NO. : 14/191677  
DATED : February 20, 2018  
INVENTOR(S) : Noriyuki Fujimori Page 1 of 1

It is certified that error appears in the above-identified patent and that said Letters Patent is hereby corrected as shown below:

Column 7, Claim 1, Lines 47 and 48 read:  
mation signal based on the first image data; in vivo information;  
Should read:  
mation signal based on the first image data;

Signed and Sealed this  
Tenth Day of July, 2018

Andrei Iancu  
*Director of the United States Patent and Trademark Office*